US008866624B2

United States Patent
Ales, III et al.

(10) Patent No.: US 8,866,624 B2
(45) Date of Patent: *Oct. 21, 2014

(54) CONDUCTOR-LESS DETECTION SYSTEM FOR AN ABSORBENT ARTICLE

(75) Inventors: Thomas Michael Ales, III, Neenah, WI (US); Sudhanshu Gakhar, Neenah, WI (US); Andrew Mark Long, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 620 days.

This patent is subject to a terminal disclaimer.

(21) Appl. No.: 12/648,645

(22) Filed: Dec. 29, 2009

(65) Prior Publication Data

US 2010/0168702 A1 Jul. 1, 2010

Related U.S. Application Data

(63) Continuation-in-part of application No. 12/347,539, filed on Dec. 31, 2008, now Pat. No. 8,274,393.

(51) Int. Cl.
| | |
|---|---|
| *G08B 21/00* | (2006.01) |
| *A61B 5/00* | (2006.01) |
| *A61B 5/20* | (2006.01) |
| *A61F 13/42* | (2006.01) |
| *A61F 13/84* | (2006.01) |
| *G01N 27/22* | (2006.01) |

(52) U.S. Cl.
CPC .............. *A61F 13/42* (2013.01); *A61B 5/6808* (2013.01); *A61B 5/202* (2013.01); *A61F 2013/8482* (2013.01); *G01N 27/223* (2013.01); *A61B 5/7207* (2013.01); *A61F 2013/424* (2013.01)

USPC ...................... 340/604; 340/573.1; 340/573.6; 340/605; 340/612; 340/620; 340/532; 340/539.1

(58) Field of Classification Search
USPC .............. 340/573.1, 573.5; 200/61.04, 61.05, 200/182; 604/361, 362, 367
See application file for complete search history.

(56) References Cited

U.S. PATENT DOCUMENTS

| | | | |
|---|---|---|---|
| 4,068,221 A | 1/1978 | McClintock | |
| 4,100,324 A | 7/1978 | Anderson et al. | |
| 4,191,950 A | 3/1980 | Levin et al. | |

(Continued)

FOREIGN PATENT DOCUMENTS

| | | |
|---|---|---|
| JP | 09-187431 A | 7/1997 |
| JP | 09-220259 A | 8/1997 |

(Continued)

*Primary Examiner* — Daniel Wu
*Assistant Examiner* — Son M Tang
(74) *Attorney, Agent, or Firm* — Kimberly-Clark Worldwide, Inc.

(57) ABSTRACT

Signaling systems are disclosed that indicate a change in an absorbent article, such as the presence of a body fluid. The various different signaling systems disclosed do not include any conductive elements contained on the interior of the article as were required in the past. Instead, the changes are monitored from the outer cover of the article. In one aspect, for instance, a signaling device is provided for sensing and indicating the presence of a body exudate in an absorbent article, the device including a housing and a capacitive sensor disposed within the housing, the capacitive sensor adapted to sense a change in capacitance due to an insult to the absorbent article. The signaling device can include an attachment mechanism for removably attaching the housing to the absorbent article.

9 Claims, 14 Drawing Sheets

(56) References Cited

U.S. PATENT DOCUMENTS

| | | | |
|---|---|---|---|
| 4,246,574 A * | 1/1981 | Sanner | 340/602 |
| 4,530,030 A * | 7/1985 | Woest et al. | 361/286 |
| 4,571,750 A | 2/1986 | Barry | |
| 4,704,108 A * | 11/1987 | Okada et al. | 604/361 |
| 4,704,116 A | 11/1987 | Enloe | |
| 4,768,023 A | 8/1988 | Xie | |
| 4,796,014 A * | 1/1989 | Chia | 340/573.5 |
| 4,800,370 A * | 1/1989 | Vetecnik | 340/573.5 |
| 4,926,871 A | 5/1990 | Ganguly et al. | |
| 4,940,464 A | 7/1990 | Van Gompel et al. | |
| 5,121,630 A | 6/1992 | Calvin | |
| 5,175,505 A * | 12/1992 | Magenau et al. | 324/671 |
| 5,284,703 A | 2/1994 | Everhart et al. | |
| 5,291,181 A * | 3/1994 | DePonte | 340/573.6 |
| 5,322,067 A | 6/1994 | Prater et al. | |
| 5,341,673 A * | 8/1994 | Burns et al. | 73/73 |
| 5,350,624 A | 9/1994 | Georger et al. | |
| 5,389,093 A | 2/1995 | Howell | |
| 5,395,358 A * | 3/1995 | Lu | 604/361 |
| 5,454,376 A | 10/1995 | Stephens et al. | |
| 5,469,145 A * | 11/1995 | Johnson | 340/604 |
| 5,469,146 A * | 11/1995 | Gurler | 340/605 |
| 5,475,835 A * | 12/1995 | Hickey | 725/109 |
| 5,486,166 A | 1/1996 | Bishop et al. | |
| 5,490,846 A | 2/1996 | Ellis et al. | |
| 5,557,263 A * | 9/1996 | Fisher et al. | 340/605 |
| 5,760,694 A * | 6/1998 | Nissim et al. | 340/604 |
| 5,766,389 A | 6/1998 | Brandon et al. | |
| 5,768,696 A * | 6/1998 | Law | 455/127.1 |
| 5,790,036 A * | 8/1998 | Fisher et al. | 340/605 |
| 5,820,973 A | 10/1998 | Dodge, II et al. | |
| 5,838,240 A | 11/1998 | Johnson | |
| 5,845,644 A | 12/1998 | Hughes et al. | |
| 5,903,222 A * | 5/1999 | Kawarizadeh et al. | 340/604 |
| 5,922,537 A * | 7/1999 | Ewart et al. | 435/6.11 |
| 6,097,297 A * | 8/2000 | Fard | 340/604 |
| 6,110,111 A | 8/2000 | Barnard | |
| 6,149,636 A * | 11/2000 | Roe et al. | 604/361 |
| 6,163,262 A | 12/2000 | Wu | |
| 6,200,250 B1 | 3/2001 | Janszen | |
| 6,246,330 B1 * | 6/2001 | Nielsen | 340/604 |
| 6,276,202 B1 | 8/2001 | Latarius | 73/335.05 |
| 6,325,066 B1 * | 12/2001 | Hughes et al. | 128/885 |
| 6,359,190 B1 | 3/2002 | Ter Ovanesyan et al. | |
| 6,372,951 B1 * | 4/2002 | Ter-Ovanesyan et al. | 604/361 |
| 6,373,263 B1 * | 4/2002 | Netzer | 324/665 |
| 6,392,542 B1 * | 5/2002 | Stanley | 340/561 |
| 6,484,053 B2 | 11/2002 | Leelamanit et al. | |
| 6,559,772 B2 * | 5/2003 | Zand et al. | 340/604 |
| 6,580,013 B1 | 6/2003 | Belloso | |
| 6,645,190 B1 | 11/2003 | Olson et al. | |
| 6,677,859 B1 * | 1/2004 | Bensen | 340/604 |
| 6,696,618 B2 * | 2/2004 | Dodge et al. | 604/367 |
| 6,731,215 B2 | 5/2004 | Harms et al. | |
| 6,756,521 B1 * | 6/2004 | Breitkopf | 604/361 |
| 6,870,479 B2 | 3/2005 | Gabriel | |
| 6,929,819 B2 | 8/2005 | Underhill et al. | |
| 7,049,969 B2 | 5/2006 | Tamai | |
| 7,141,715 B2 * | 11/2006 | Shapira | 604/361 |
| 7,394,391 B2 | 7/2008 | Long | |
| 7,477,156 B2 | 1/2009 | Long et al. | |
| 7,489,252 B2 * | 2/2009 | Long et al. | 340/604 |
| 7,492,270 B2 * | 2/2009 | Veerasamy | 340/602 |
| 7,731,665 B2 * | 6/2010 | Lee et al. | 600/501 |
| 7,812,731 B2 * | 10/2010 | Bunza et al. | 340/573.5 |
| 7,833,177 B2 | 11/2010 | Long et al. | |
| 8,098,900 B2 * | 1/2012 | Determan et al. | 382/115 |
| 2002/0026164 A1 | 2/2002 | Camarero et al. | |
| 2003/0028165 A1 | 2/2003 | Curro et al. | |
| 2003/0060789 A1 | 3/2003 | Shapira et al. | |
| 2004/0147888 A1 * | 7/2004 | Huang et al. | 604/361 |
| 2004/0220538 A1 * | 11/2004 | Panopoulos | 604/361 |
| 2004/0236302 A1 | 11/2004 | Wilhelm et al. | |
| 2005/0046578 A1 * | 3/2005 | Pires | 340/573.5 |
| 2005/0156744 A1 | 7/2005 | Pires | |
| 2005/0195085 A1 | 9/2005 | Cretu-Petra | |
| 2005/0251036 A1 | 11/2005 | Abuhamad | |
| 2006/0069360 A1 | 3/2006 | Long et al. | |
| 2006/0174693 A1 | 8/2006 | Chen et al. | |
| 2006/0258916 A1 | 11/2006 | Pietersen | |
| 2007/0024457 A1 | 2/2007 | Long et al. | |
| 2007/0048709 A1 | 3/2007 | Ales et al. | |
| 2007/0142797 A1 | 6/2007 | Long et al. | |
| 2007/0142799 A1 | 6/2007 | Ales et al. | |
| 2007/0252712 A1 | 11/2007 | Allen et al. | |
| 2008/0041792 A1 | 2/2008 | Crnkovich et al. | |
| 2008/0048786 A1 | 2/2008 | Feldkamp et al. | |
| 2008/0054408 A1 | 3/2008 | Tippey et al. | |
| 2008/0077040 A1 | 3/2008 | Ales et al. | |
| 2008/0077042 A1 | 3/2008 | Feldkamp et al. | |
| 2008/0132859 A1 | 6/2008 | Pires | |
| 2008/0145947 A1 | 6/2008 | Boga et al. | |
| 2008/0243099 A1 | 10/2008 | Tippey et al. | |
| 2008/0262376 A1 | 10/2008 | Price | |
| 2008/0266122 A1 | 10/2008 | Ales et al. | |
| 2008/0278337 A1 * | 11/2008 | Huang et al. | 340/573.5 |
| 2008/0284608 A1 | 11/2008 | Long | |
| 2008/0306461 A1 * | 12/2008 | Jan | 604/361 |
| 2009/0005748 A1 | 1/2009 | Ales et al. | |
| 2009/0062756 A1 | 3/2009 | Long et al. | |
| 2009/0157025 A1 | 6/2009 | Song et al. | |
| 2009/0326417 A1 | 12/2009 | Ales, III et al. | |
| 2010/0114047 A1 | 5/2010 | Song et al. | |
| 2013/0324955 A1 * | 12/2013 | Wong et al. | 604/361 |

FOREIGN PATENT DOCUMENTS

| | | |
|---|---|---|
| JP | 09-290001 A | 11/1997 |
| JP | 2001-318067 A | 11/2001 |
| JP | 2002-071584 A | 3/2002 |
| JP | 2002-153497 A | 5/2002 |
| JP | 2005-013244 A | 1/2005 |
| JP | 2006-043389 A | 2/2006 |
| KR | 10-2009-0081886 A | 7/2009 |
| WO | WO 00/37009 A2 | 6/2000 |
| WO | WO 01/18535 A2 | 3/2001 |
| WO | WO 2005/106465 A1 | 11/2005 |
| WO | WO 2010/123425 A1 | 10/2010 |

* cited by examiner

CONDUCTOR-LESS DETECTION SYSTEM FOR AN ABSORBENT ARTICLE

RELATED APPLICATIONS

The present application is a continuation-in-part of U.S. patent application Ser. No. 12/347,539, filed on Dec. 31, 2008, now U.S. Pat. No. 8,274,393 entitled "Remote Detection Systems for Absorbent Articles."

BACKGROUND

Absorbent articles such as diapers, training pants, incontinence products, feminine hygiene products, swim undergarments, and the like, conventionally include a liquid permeable body-side liner, a liquid impermeable outer cover, and an absorbent structure. The absorbent structure is typically located between the outer cover and the liner for taking in and retaining liquids (e.g., urine) exuded by the wearer. The absorbent structure can be made of, for instance, superabsorbent particles. Many absorbent articles, especially those sold under the trade name HUGGIES by the Kimberly-Clark Corporation, are so efficient at absorbing liquids that it is sometimes difficult to tell whether or not the absorbent article has been insulted with a body exudate, especially when the absorbent article is being worn by a newborn or other very young wearers. Insult amounts in such wearers tend to be very small. Other wearers might also produce very small insults.

Accordingly, various types of moisture or wetness indicators have been suggested for use in absorbent articles. The wetness indicators include various passive indicators such as indicator strips, printing, or other devices within each absorbent article, requiring a caregiver to pay for the wetness indicator in each absorbent article whether or not the caregiver intends to use the wetness indicator. Wetness indicators can also include alarm devices that are designed to assist parents or attendants in identifying a wet absorbent article condition early on. The devices can produce an audible, tactile, electromagnetic, or visual signal. Many of these devices rely on electronics, including conductive elements within each absorbent article that can increase the expense of the absorbent article.

In some aspects, for instance, conductive threads or foils have been placed in the absorbent articles that extend from the front of the article to the back of the article. The conductive materials serve as conductive leads for a signaling device and form an open circuit in the article that can be closed when a body fluid, such as urine, closes the circuit.

Incorporating conductive leads into absorbent articles, however, has caused various problems. For example, absorbent articles are typically mass produced on very fast moving machinery. Incorporating conductive leads into an absorbent article at conventional machine speeds has been problematic.

In addition, packaged absorbent articles are typically fed through a metal detector to ensure that there are no foreign objects contained in the package. If the conductive leads are made from or contain a metal, the metal detector can be activated registering a false positive. The incorporation of metallic materials into absorbent articles can also cause problems for those wearing the garments when attempting to pass through security gates that include metal detectors.

In view of the above, a need currently exists for a signaling system for an absorbent article that does not require conductive elements containing metal or other devices to be inserted into the interior of the article.

SUMMARY

The present inventors undertook intensive research and development efforts with respect to improving absorbent articles, particularly in providing a wetness indicator only when desired by a caregiver and without adding to the cost of an absorbent article. A need exists for wetness detection in absorbent articles and incontinence products in general. Technology that can be implemented without altering absorbent article construction is preferred.

A non-invasive sensor measures electrical capacitance at some depth within an absorbent article. A useful approach is a capacitive sensor that can be attached to an appropriate target zone on the outer cover of the absorbent article.

The present disclosure is generally directed to various signaling systems that are particularly well suited for use in conjunction with absorbent articles. The signaling systems, for instance, can be connected to a signaling device that can be configured to emit a signal, such as an audible, tactile, electromagnetic or visual signal, for indicating to a user that a body fluid is present in the absorbent article. For example, in one aspect, the absorbent article includes a diaper and the signaling system is configured to indicate the presence of urine or a bowel movement. In other absorbent articles, however, the signaling systems can be configured to indicate the presence of yeast or metabolites.

More particularly, the present disclosure is directed to signaling systems for absorbent articles that can detect the presence of a body fluid without having to place or insert conductive elements into the interior of the article. For instance, in one aspect, a sensor can be mounted to an exterior surface of the absorbent article that is capable of sensing a change on the interior of the article that indicates the presence of a body fluid, such as urine, which is a conductive fluid. In this aspect, the sensor can include, for instance, a capacitive sensor. Insulting the absorbent article with urine will create a change in capacitance. The sensor can be placed in communication with a signaling device. Once a change within the interior of the absorbent article is detected, the signaling device can be configured to emit a signal that indicates a body fluid is present in the absorbent article.

Other features and aspects of the present disclosure are discussed in greater detail herein.

BRIEF DESCRIPTION OF THE DRAWINGS

The foregoing and other features and aspects of the present disclosure and the manner of attaining them will become more apparent, and the disclosure itself will be better understood by reference to the following description, appended claims, and accompanying drawings.

Figure 1:
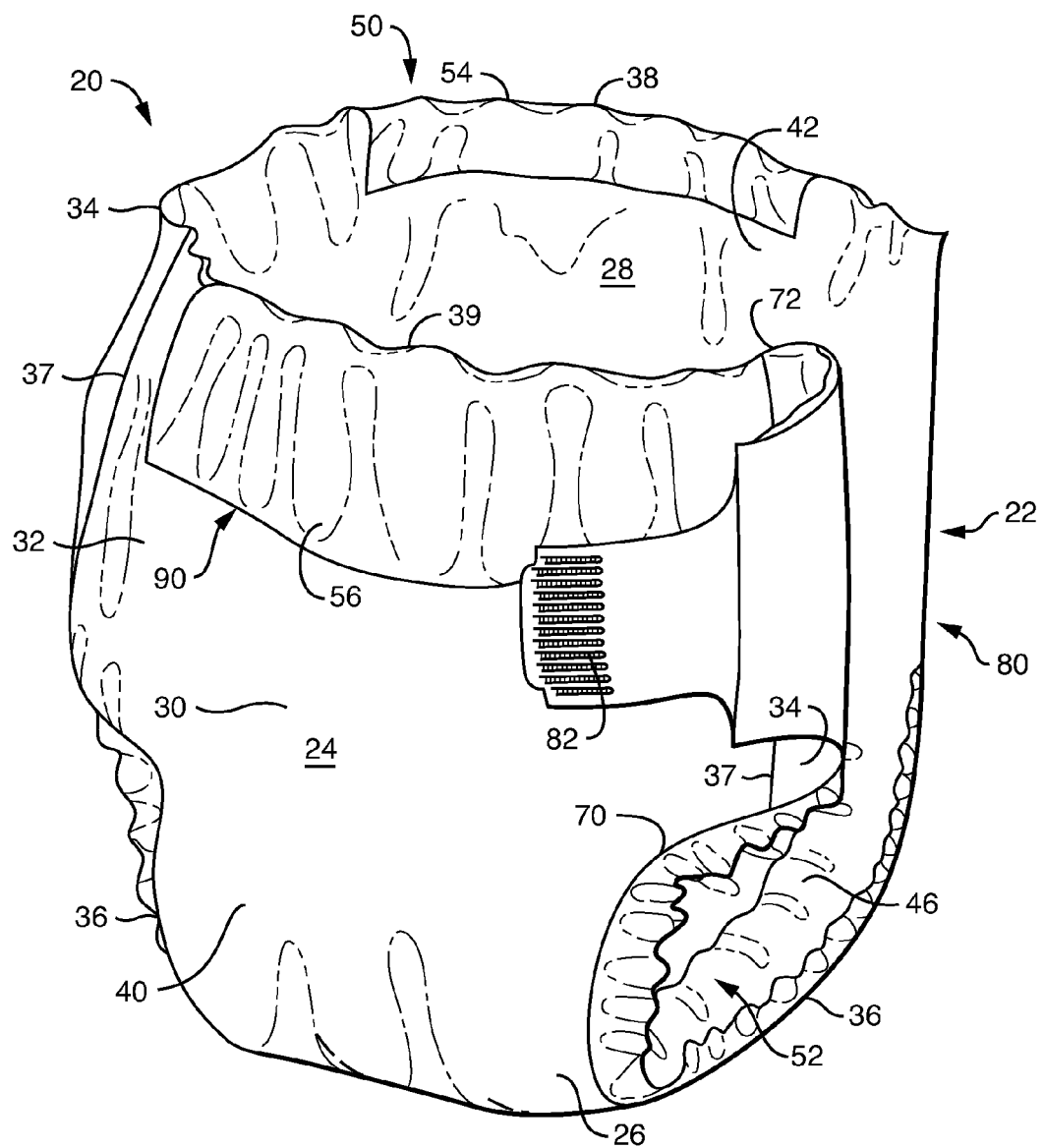
FIG. 1 is a rear perspective view of one aspect of an absorbent article.

Repeat use of reference characters in the present specification and drawings is intended to represent the same or analogous features or elements of the present disclosure.

DETAILED DESCRIPTION

It is to be understood by one of ordinary skill in the art that the present discussion is a description of exemplary aspects only, and is not intended as limiting the broader aspects of the present disclosure.

The present disclosure is generally directed to signaling systems for absorbent articles that indicate to a user when a body fluid has insulted the article. For example, in one aspect, the signaling system is designed to emit a signal when urine is detected in the absorbent article. Of particular advantage, signaling systems made in accordance with the present disclosure can sense the presence of a body fluid within the absorbent article without having to construct the absorbent article with any elements or sensors contained in the interior of the article. In the past, for instance, metallic conductive leads were typically placed within the interior of the absorbent article. The signaling systems of the present disclosure, on the other hand, can sense the presence of a body fluid from an exterior surface of the article that can greatly simplify the incorporation of the signaling system into the article.

Figure 2:
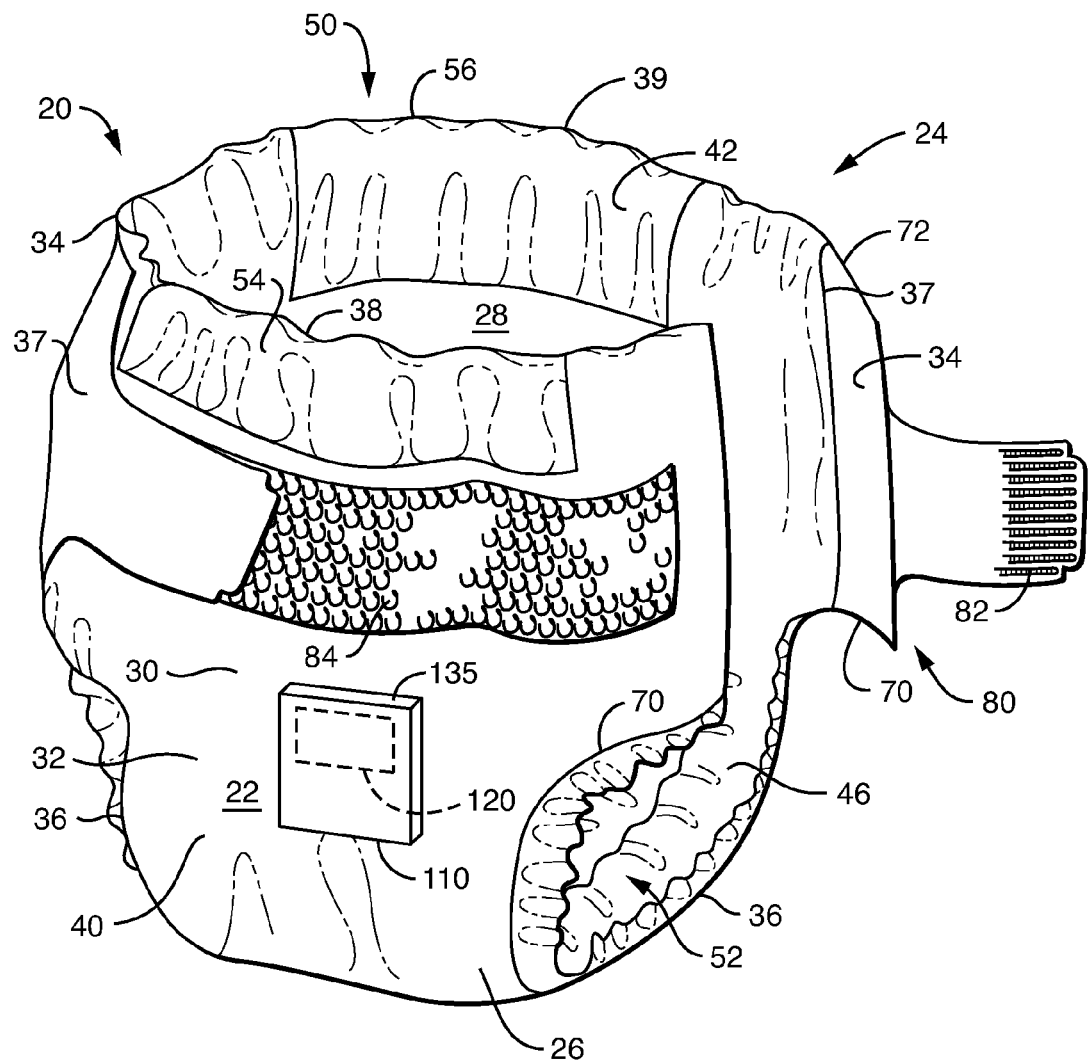
FIG. 2 is a front perspective view of the absorbent article illustrated in FIG. 1 including one aspect of a wetness indicator of the present disclosure.

In accordance with the present disclosure, the signaling system can have various configurations and designs. Referring to FIGS. 1 and 2, for exemplary purposes, an absorbent article 20 that can be used in conjunction with signaling systems of the present disclosure, is shown. The absorbent article 20 can be disposable or not. It is understood that the present disclosure is suitable for use with various other absorbent articles intended for personal wear, including but not limited to diapers, training pants, swim pants, feminine hygiene products, incontinence products, medical garments, surgical pads and bandages, other personal care or health care garments, and the like without departing from the scope of the present disclosure.

By way of illustration only, various materials and methods for constructing absorbent articles such as the absorbent article 20 of the various aspects of the present disclosure are disclosed in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference to the extent they are consistent (i.e., not in conflict) herewith.

Figure 3:
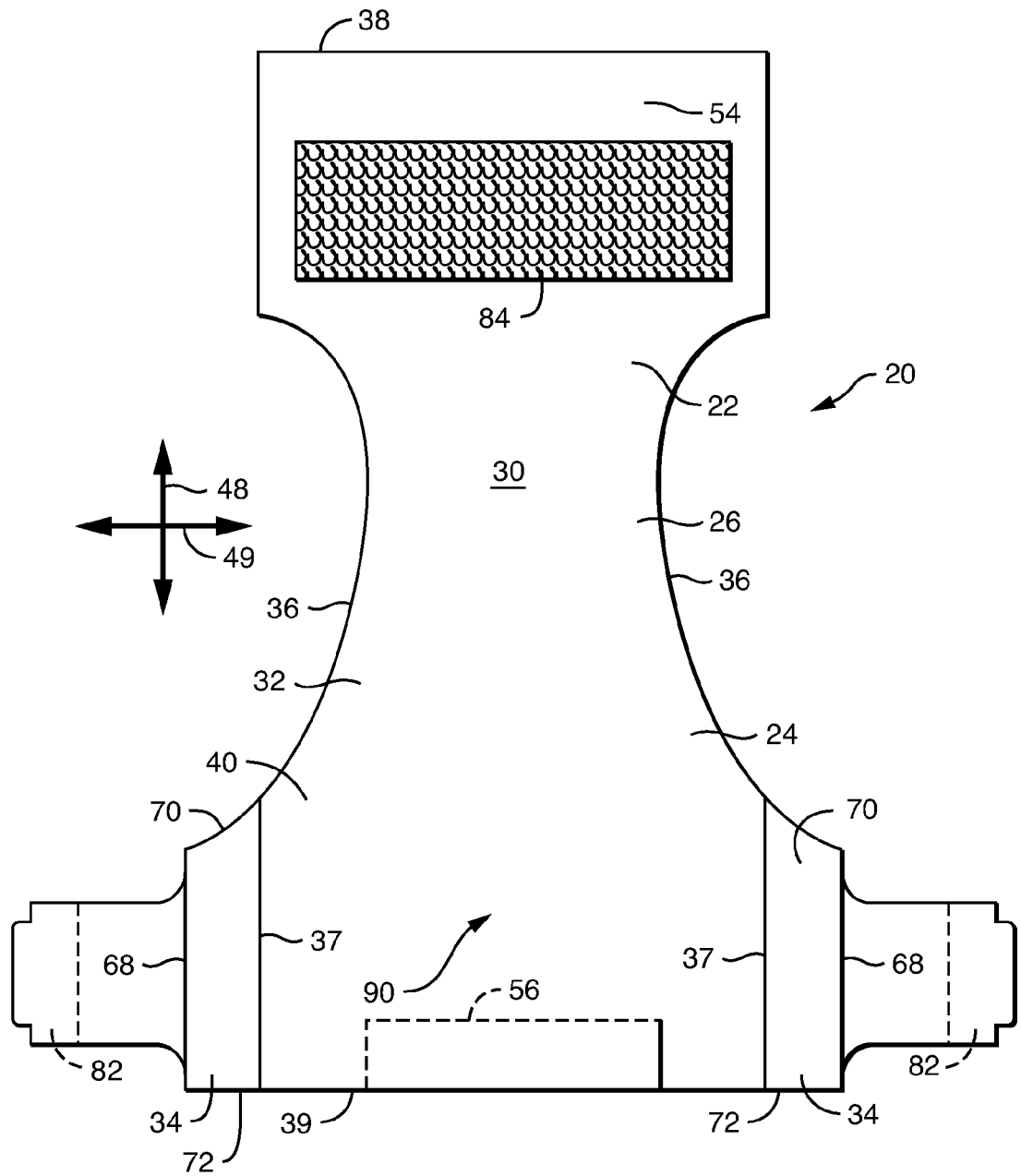
FIG. 3 is a plan view of the absorbent article shown in FIG. 1 with the article in an unfastened, unfolded and laid flat condition showing the surface of the article that faces away from the wearer.
Figure 4:
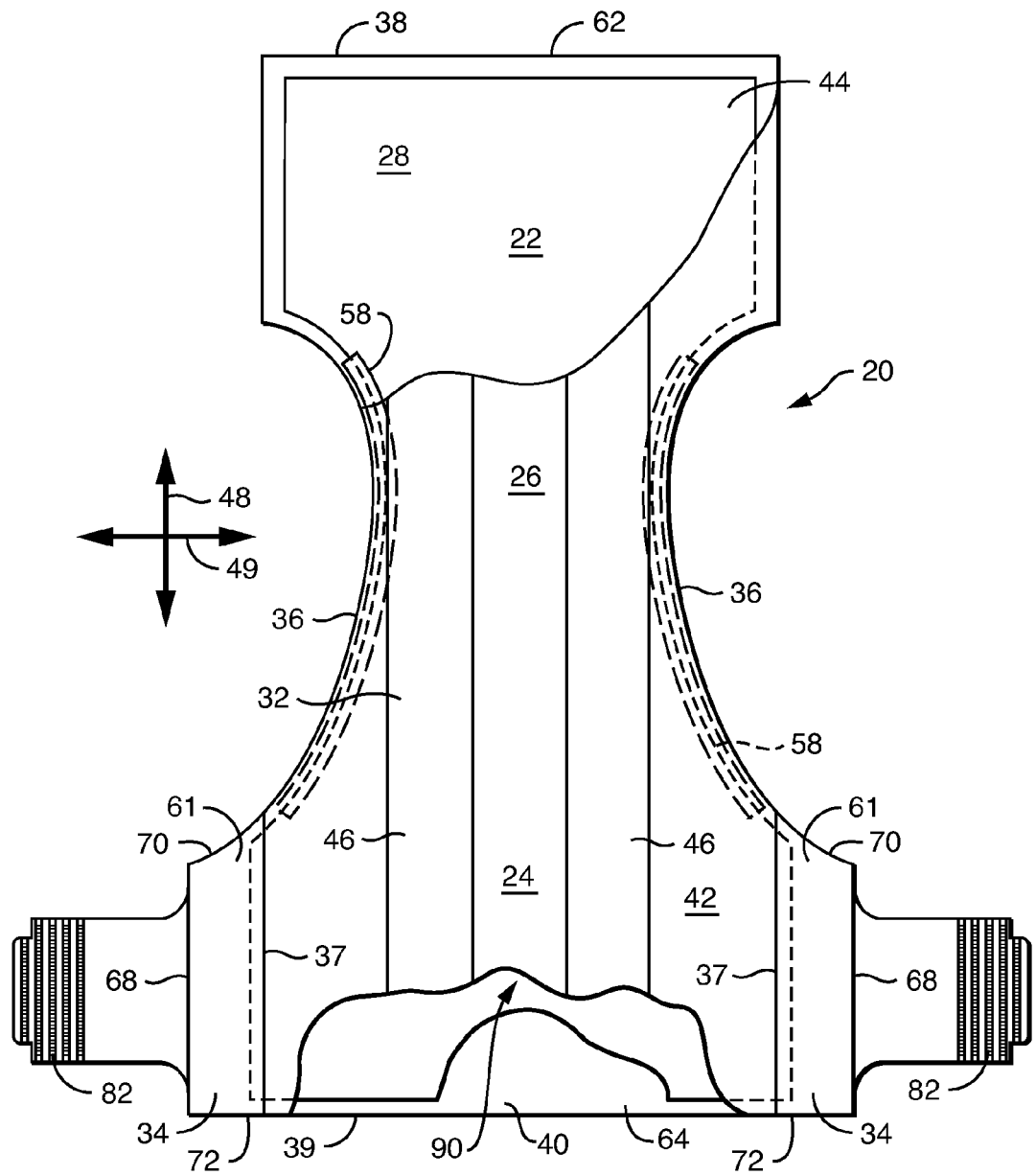
FIG. 4 is a plan view similar to FIG. 3 showing the surface of the absorbent article that faces the wearer when worn and with portions cut away to show underlying features.

An absorbent article 20 is representatively illustrated in FIG. 1 in a partially fastened condition. The absorbent article 20 shown in FIGS. 1 and 2 is also represented in FIGS. 3 and 4 in an opened and unfolded state. Specifically, FIG. 3 is a plan view illustrating the exterior side of the absorbent article 20, while FIG. 4 illustrates the interior side of the absorbent article 20. As shown in FIGS. 3 and 4, the absorbent article 20 defines a longitudinal direction 48 that extends from the front of the article when worn to the back of the article. Orthogonal to the longitudinal direction 48 is a lateral direction 49.

The absorbent article 20 defines a pair of longitudinal end regions, otherwise referred to herein as a front region 22 and a back region 24, and a center region, otherwise referred to herein as a crotch region 26, extending longitudinally between and interconnecting the front and back regions 22, 24. The absorbent article 20 also defines an inner surface 28 adapted in use (e.g., positioned relative to the other components of the article 20) to be disposed toward the wearer, and an outer surface 30 opposite the inner surface. The front and back regions 22, 24 are those portions of the absorbent article 20, that, when worn, wholly or partially cover or encircle the waist or mid-lower torso of the wearer. The crotch region 26 generally is that portion of the absorbent article 20 that, when worn, is positioned between the legs of the wearer and covers the lower torso and crotch of the wearer. The absorbent article 20 has a pair of laterally opposite side edges 36 and a pair of longitudinally opposite waist edges, respectively designated front waist edge 38 and back waist edge 39.

The illustrated absorbent article 20 includes a chassis 32 that, in this aspect, encompasses the front region 22, the back region 24, and the crotch region 26. Referring to FIGS. 1-4, the chassis 32 includes an outer cover 40 and a bodyside liner 42 (FIGS. 1 and 4) that can be joined to the outer cover 40 in a superimposed relation therewith by adhesives, ultrasonic bonds, thermal bonds or other conventional techniques. Referring to FIG. 4, the liner 42 can suitably be joined to the outer cover 40 along the perimeter of the chassis 32 to form a front waist seam 62 and a back waist seam 64. As shown in FIG. 4, the liner 42 can suitably be joined to the outer cover 40 to form a pair of side seams 61 in the front region 22 and the back region 24. The liner 42 can be generally adapted, i.e., positioned relative to the other components of the article 20, to be disposed toward the wearer's skin during wear of the absorbent article 20. The chassis 32 can further include an absorbent structure 44 particularly shown in FIG. 4 disposed between the outer cover 40 and the bodyside liner 42 for absorbing liquid body exudates exuded by the wearer, and can further include a pair of containment flaps 46 secured to the bodyside liner 42 for inhibiting the lateral flow of body exudates.

The elasticized containment flaps 46 as shown in FIG. 4 define a partially unattached edge that assumes an upright configuration in at least the crotch region 26 of the absorbent article 20 to form a seal against the wearer's body. The containment flaps 46 can extend longitudinally along the entire length of the chassis 32 or can extend only partially along the length of the chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the absorbent article 20 can also suitably include leg elastic members 58 (FIG. 4), as are known to those skilled in the art. The leg elastic members 58 can be operatively joined to the outer cover 40 and/or the bodyside liner 42 and positioned in the crotch region 26 of the absorbent article 20.

The leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example, with the application of heat, such that elastic retractive forces are imparted to the substrate. In one particular aspect, for example, the leg elastic members 58 can include a plurality of dry-spun coalesced multifilament spandex elastomeric threads sold under the trade name LYCRA and available from Invista, Wilmington, Del., U.S.A.

In some aspects, the absorbent article 20 can further include a surge management layer (not shown) that can be optionally located adjacent the absorbent structure 44 and attached to various components in the article 20 such as the absorbent structure 44 or the bodyside liner 42 by methods known in the art, such as by using an adhesive. A surge management layer helps to decelerate and diffuse surges or gushes of liquid that can be rapidly introduced into the absorbent structure of the article. Desirably, the surge management layer can rapidly accept and temporarily hold the liquid prior to releasing the liquid into the storage or retention portions of the absorbent structure. Examples of suitable surge management layers are described in U.S. Pat. No. 5,486,166; and U.S. Pat. No. 5,490,846. Other suitable surge management materials are described in U.S. Pat. No. 5,820,973. The entire disclosures of these patents are hereby incorporated by reference herein to the extent they are consistent (i.e., not in conflict) herewith.

As shown in FIGS. 1-4, the absorbent article 20 further includes a pair of opposing elastic side panels 34 that are attached to the back region of the chassis 32. As shown particularly in FIGS. 1 and 2, the side panels 34 can be stretched around the waist and/or hips of a wearer to secure the garment in place. As shown in FIGS. 3 and 4, the elastic side panels are attached to the chassis along a pair of opposing longitudinal edges 37. The side panels 34 can be attached or bonded to the chassis 32 using any suitable bonding technique. For instance, the side panels 34 can be joined to the chassis by adhesives, ultrasonic bonds, thermal bonds, or other conventional techniques.

In an alternative aspect, the elastic side panels can also be integrally formed with the chassis 32. For instance, the side panels 34 can include an extension of the bodyside liner 42, of the outer cover 40, or of both the bodyside liner 42 and the outer cover 40.

In the aspects shown in the figures, the side panels 34 are connected to the back region of the absorbent article 20 and extend over the front region of the article when securing the article in place on a user. It should be understood, however, that the side panels 34 can alternatively be connected to the front region of the article 20 and extend over the back region when the article is donned.

With the absorbent article 20 in the fastened position as partially illustrated in FIGS. 1 and 2, the elastic side panels 34 can be connected by a fastening system 80 to define a 3-dimensional absorbent article configuration having a waist opening 50 and a pair of leg openings 52. The waist opening 50 of the article 20 is defined by the waist edges 38 and 39 that encircle the waist of the wearer.

In the aspects shown in the figures, the side panels are releasably attachable to the front region 22 of the article 20 by the fastening system. It should be understood, however, that in other aspects the side panels can be permanently joined to the chassis 32 at each end. The side panels can be permanently bonded together, for instance, when forming a training pant or absorbent swimwear.

The elastic side panels 34 each have a longitudinal outer edge 68, a leg end edge 70 disposed toward the longitudinal center of the absorbent article 20, and waist end edges 72 disposed toward a longitudinal end of the absorbent article. The leg end edges 70 of the absorbent article 20 can be suitably curved and/or angled relative to the lateral direction 49 to provide a better fit around the wearer's legs. However, it is understood that only one of the leg end edges 70 can be curved or angled, such as the leg end edge of the back region 24, or alternatively, neither of the leg end edges can be curved or angled, without departing from the scope of the present disclosure. As shown in FIG. 4, the outer edges 68 are generally parallel to the longitudinal direction 48 while the waist end edges 72 are generally parallel to the transverse axis 49. It should be understood, however, that in other aspects the outer edges 68 and/or the waist edges 72 can be slanted or curved as desired. Ultimately, the side panels 34 are generally aligned with a waist region 90 of the chassis.

The fastening system 80 can include laterally opposite first fastening components 82 adapted for refastenable engagement to corresponding second fastening components 84. In the aspect shown in the figures, the first fastening component 82 is located on the elastic side panels 34, while the second fastening component 84 is located on the front region 22 of the chassis 32. In one aspect, a front or outer surface of each of the fastening components 82, 84 includes a plurality of engaging elements. The engaging elements of the first fastening components 82 are adapted to repeatedly engage and disengage corresponding engaging elements of the second fastening components 84 to releasably secure the article 20 in its three-dimensional configuration.

The fastening components 82, 84 can be any refastenable fasteners suitable for absorbent articles, such as adhesive fasteners, cohesive fasteners, mechanical fasteners, or the like. In particular aspects, the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated aspect, the first fastening components 82 include hook fasteners and the second fastening components 84 include complementary loop fasteners. Alternatively, the first fastening components 82 can include loop fasteners and the second fastening components 84 can be complementary hook fasteners. In another aspect, the fastening components 82, 84 can be interlocking similar surface fasteners, or adhesive and cohesive fastening elements such as an adhesive fastener and an adhesive-receptive landing zone or material; or the like.

In addition to possibly having elastic side panels, the absorbent article 20 can include various waist elastic members for providing elasticity around the waist opening. For example, as shown in the figures, the absorbent article 20 can include a front waist elastic member 54 and/or a back waist elastic member 56.

Figure 5:
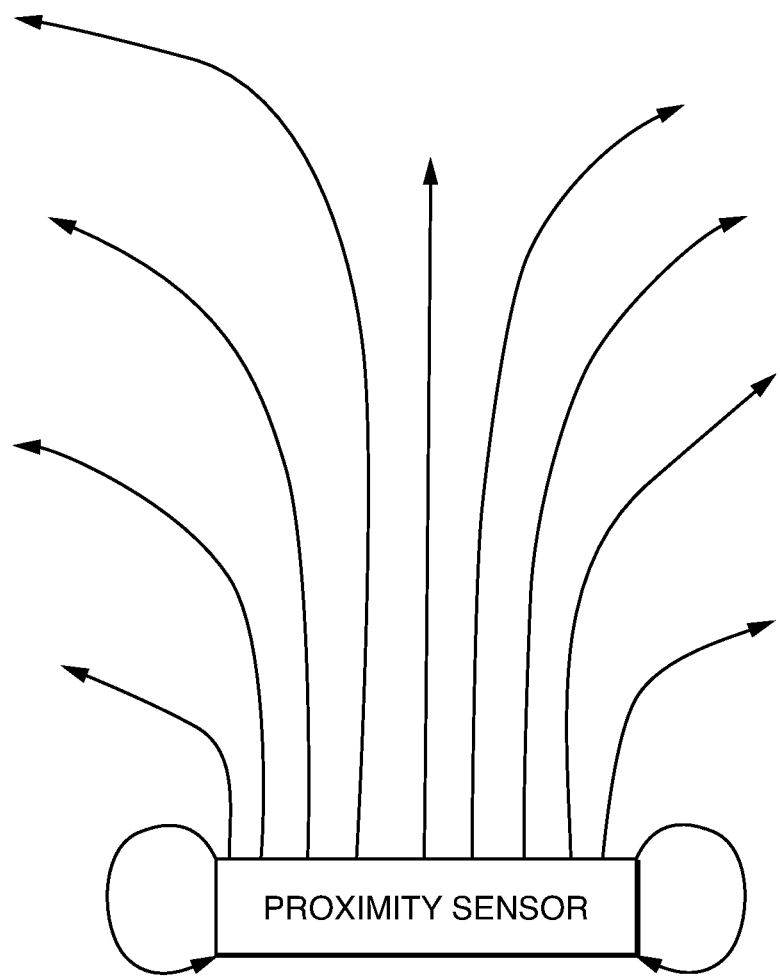
FIG. 5 is a schematic view of the electric field created by an open face virtual capacitor when energized, as used in the wetness indicator of the present disclosure.

In one aspect of the present disclosure best illustrated in FIG. 2, a signaling device 110 includes a capacitive sensor 120 that is adapted to detect the presence of a body exudate in the absorbent article 20. A noninvasive capacitive-based touch sensor can be used to determine the permittivity of material near the sensing element. The sensing element can take the form of an open face virtual capacitor that, when energized, creates an electric field such as that illustrated in FIG. 5.

The capacitive sensor 120 includes a capacitive touch sensing means. The capacitive touch sensing means can include two electrodes creating an electrostatic field that extends beyond the face of the antenna or electrodes, in this case beyond the face of the signaling device 110. Conductive substances such as body exudates in the absorbent article 20 act as dielectrics that change field dynamics, causing a load on the system. This load amount can be read as merely the presence or the extent of the presence of moisture, for example. Construction and the power applied to the electrodes can control the extent to which the field extends and the frequency of the power can be adjusted to fine tune selectivity to certain dielectrics.

For example, a noninvasive, capacitive-based touch sensor can be used to determine the permeability of material near the sensing element. The sensing element can take a form of an inter-digitized electrode forming an open-face virtual capacitor. Similar technology has been used to determine moisture content in soil and in touch sensors such as key pads, thumbwheels, etc. As described herein, this technology can be applied to detect wetness in an absorbent article from outside the outer cover. Key challenges, however, with such a capacitive touch sensing system are managing the penetration depth of the electric field and the ability of the system to detect a small amount of wetness from outside the outer cover. Such challenges can be resolved through signal conditioning and developing algorithms to ignore environmental interferences, as described below.

Figure 6:
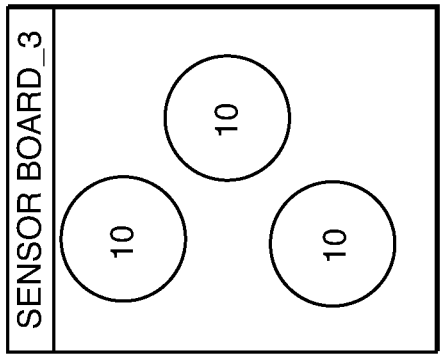
FIG. 6 is a schematic view of several array geometries that can be used for a capacitive sensing array, as used in the wetness indicator of the present disclosure.
Figure 6:
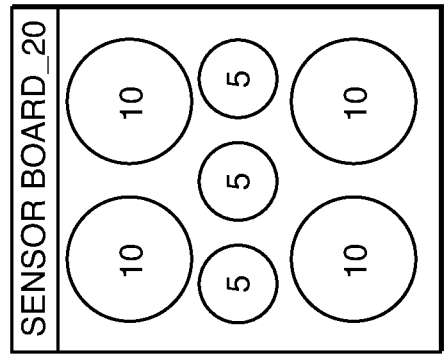
Figure 6:
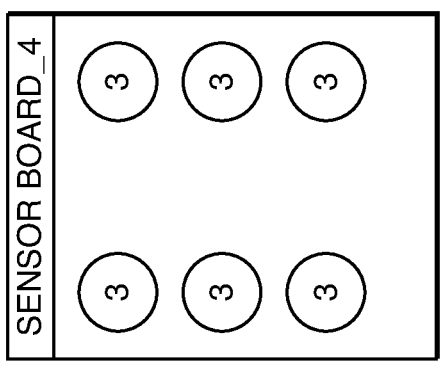
Figure 6:
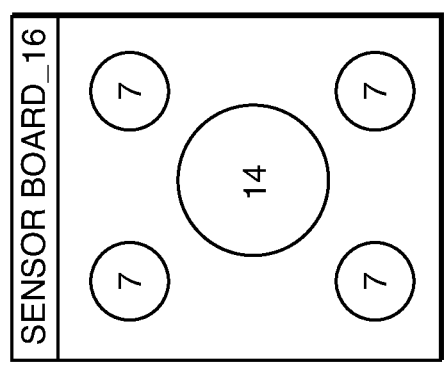
Figure 6:
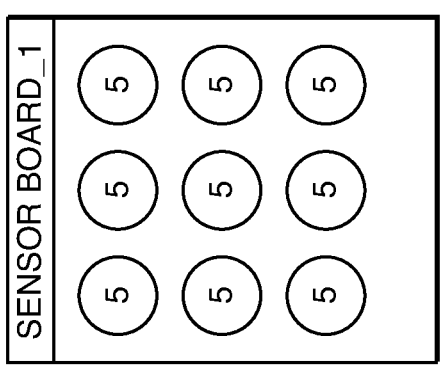
Figure 6:
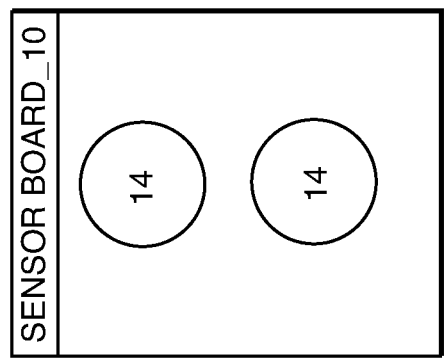

Sensor design is important in determining the sensitivity of the capacitive sensor 120 to detect wetness in the absorbent article 20. Some of the important parameters include the diameter of the capacitor pad, for example from 5 to 15 mm, the number of capacitors in one array, for example from 1 to 10, and the spacing between the capacitor and the ground plane, for example from 1 mm to 2.5 mm. A ground plane can be positioned at the back of the sensor to prevent interference from the back side of the sensor. There are several array geometries that can be used for a capacitive sensing array, including but not limited to those illustrated in FIG. 6.

Figure 7:
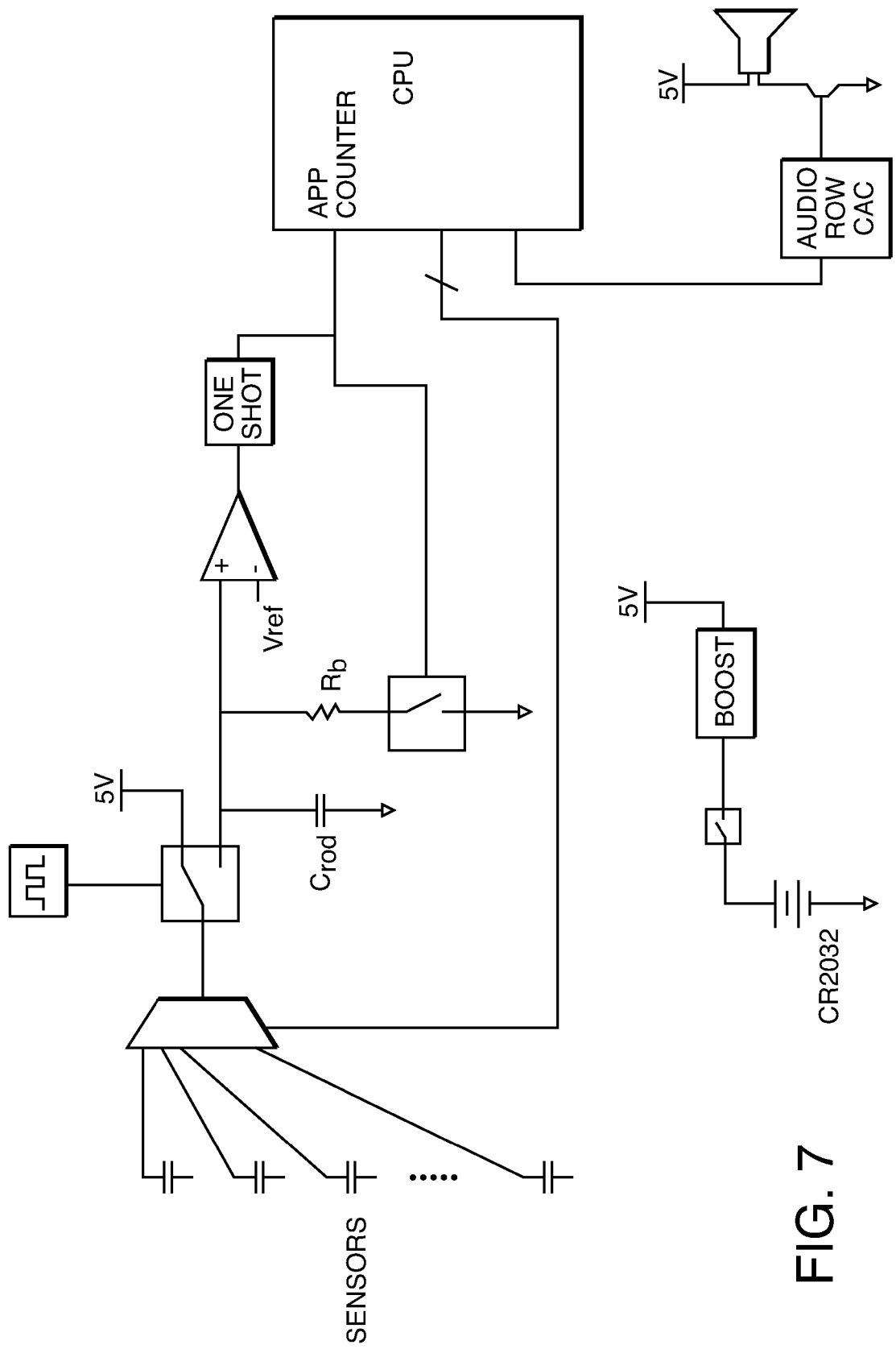
FIG. 7 is a schematic view of one method of providing a wetness indicator of the present disclosure.

In various aspects of the present disclosure, different methods can be used in constructing a capacitive sensor 120. In a first method illustrated in FIG. 7, the sensor 120 can be viewed as a constant capacitance sensor because the sensor size and distance to the ground plane cannot change. Any parasitic capacitance, either trace capacitance, IC capacitance, or ADC capacitance, can be said to be constant. When the sensor is in open air, it is a parallel plate capacitor, with one side seeing electric fields normal to the ground plane below it. There is slight fringing to the adjacent ground plane.

When an absorbent article 20 or any material with a higher dielectric than air is present on the top of the sensor 120, the fringing fields present when air was only present now spread into the higher dielectric material and have a better path to a lower potential or ground. This increases the capacitance and can be detected using the ADC. When water is present in the absorbent article 20, the dielectric constant now increases much more than when an absorbent article 20 or other dielectric was present. Water has a dielectric greater than 50 and now provides a better path for the electric fields to a lower potential or ground.

One example of a system design for this method includes a microcontroller made by Microchip Inc., part number PIC24FJ128GA106, which has a dedicated charge time measurement unit (CTMU). The CTMU is a module add-on to the microcontroller that can be used directly to detect changes in capacitance. In this system design, an array of capacitor sensors are attached to the A/D inputs of the Microchip PIC 24FJ series microcontroller and used to compute the changes in capacitance as the dielectric changes in presence of wetness.

Figure 8:
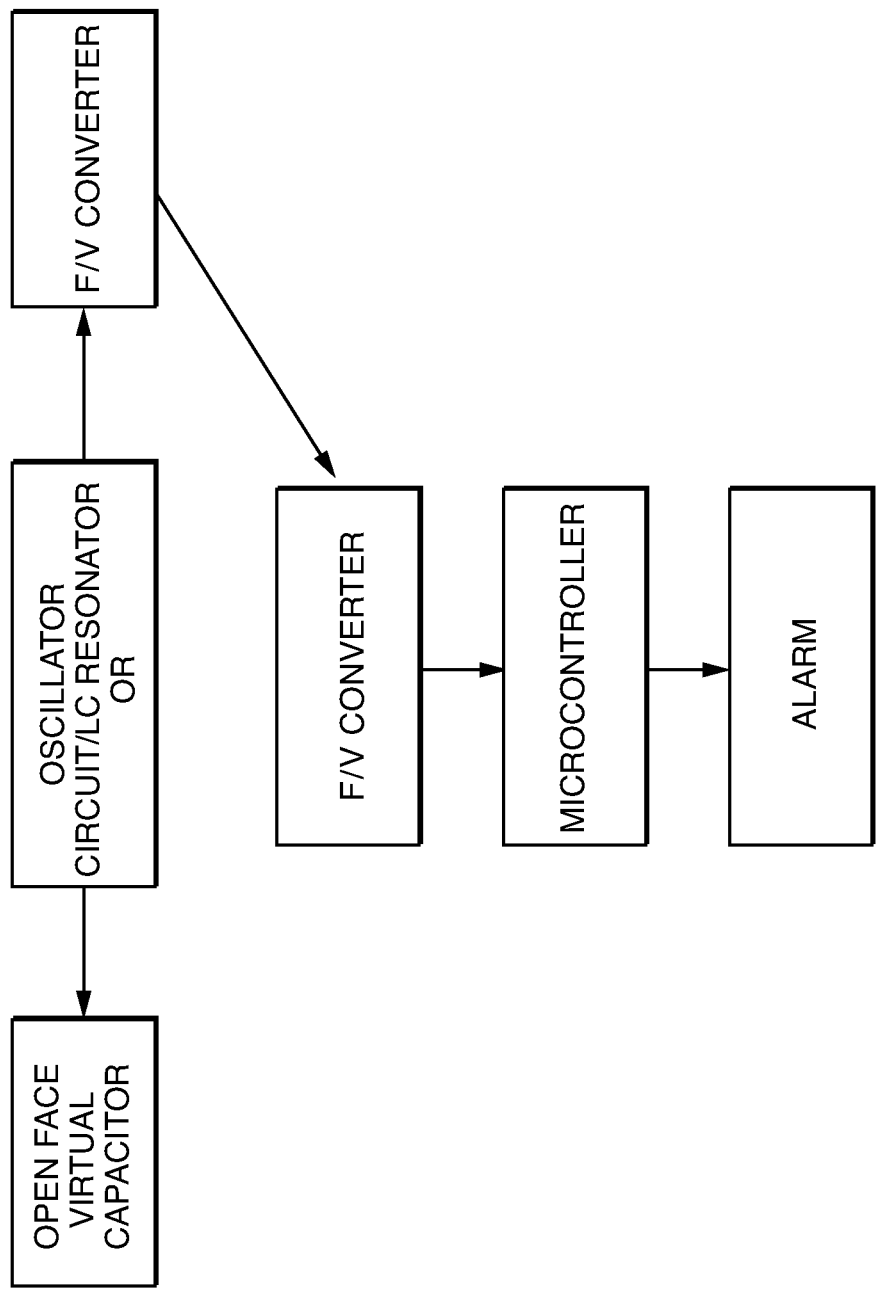
FIG. 8 is a block diagram of an alternate method of providing a wetness indicator of the present disclosure.

In a second method, changes are detected in the resonant frequency of an LC circuit. As the capacitance value of the resonator circuit changes the frequency of the oscillating frequency of the resonator changes, this can be detected by a frequency-to-voltage (F/V) converting chip such as TC 9400 made by Microchip Technologies Inc. of Chandler, Ariz. U.S.A. The F/V converter produces a voltage used by a microcontroller. When a voltage setpoint is reached, as determined by the microcontroller, an alarm signal is generated as further described herein. A block diagram of such a system is illustrated in FIG. 8.

Figure 9:
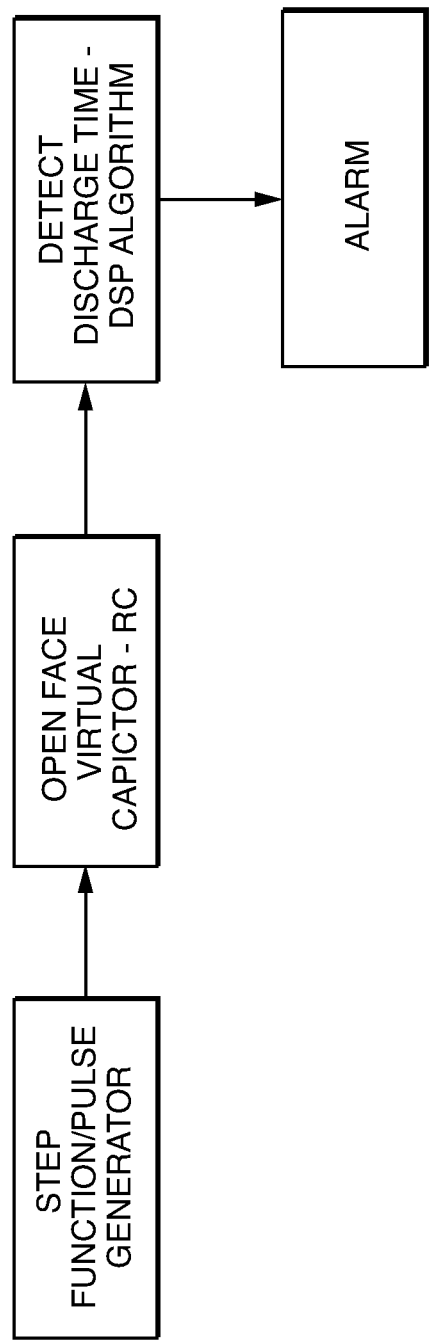
FIG. 9 is a block diagram of an alternate method of providing a wetness indicator of the present disclosure.
Figure 10A:
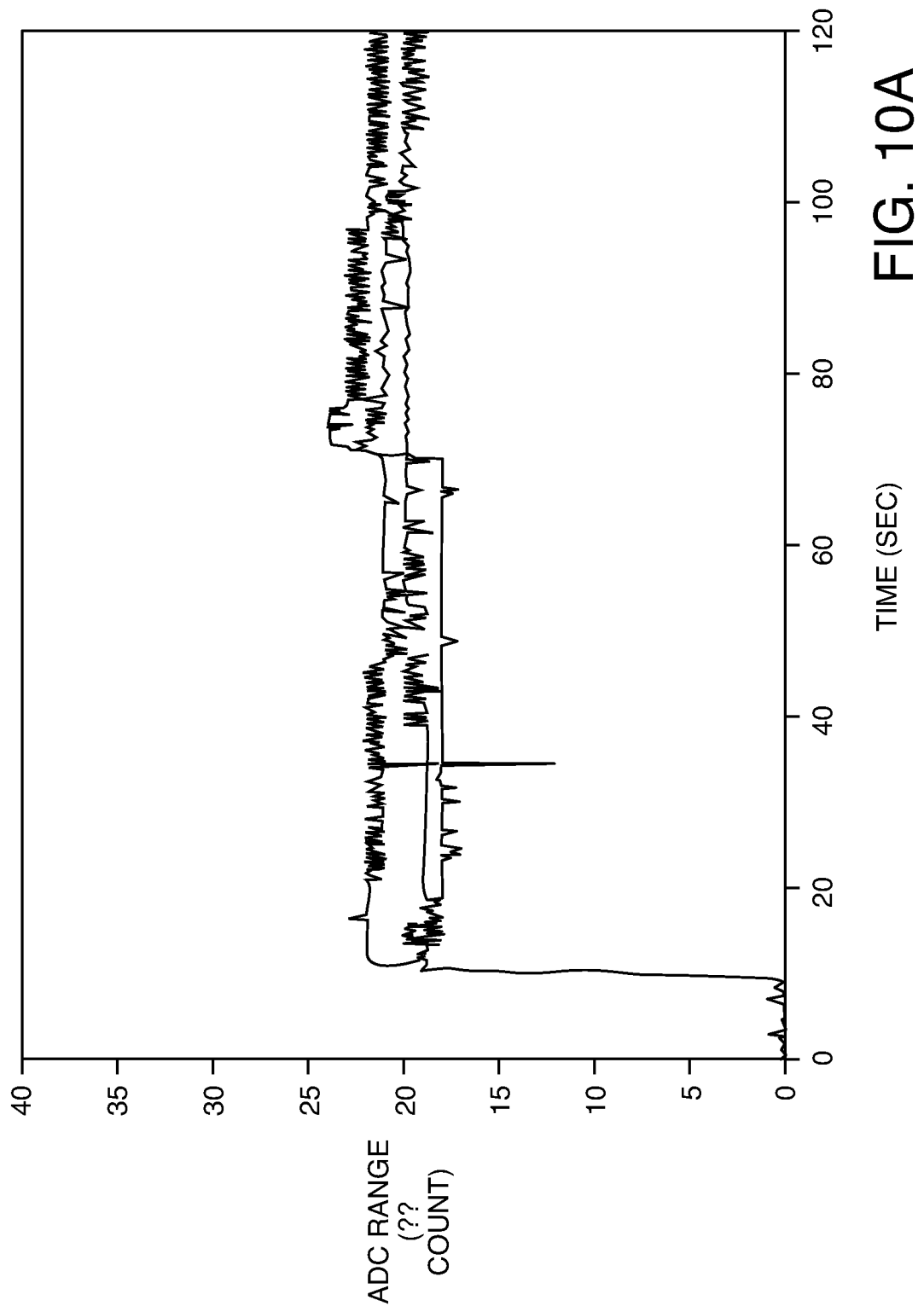
FIG. 10 illustrates a representative set of sensor data in which a change in capacitance is detected using a wetness indicator of the present disclosure.
Figure 10B:
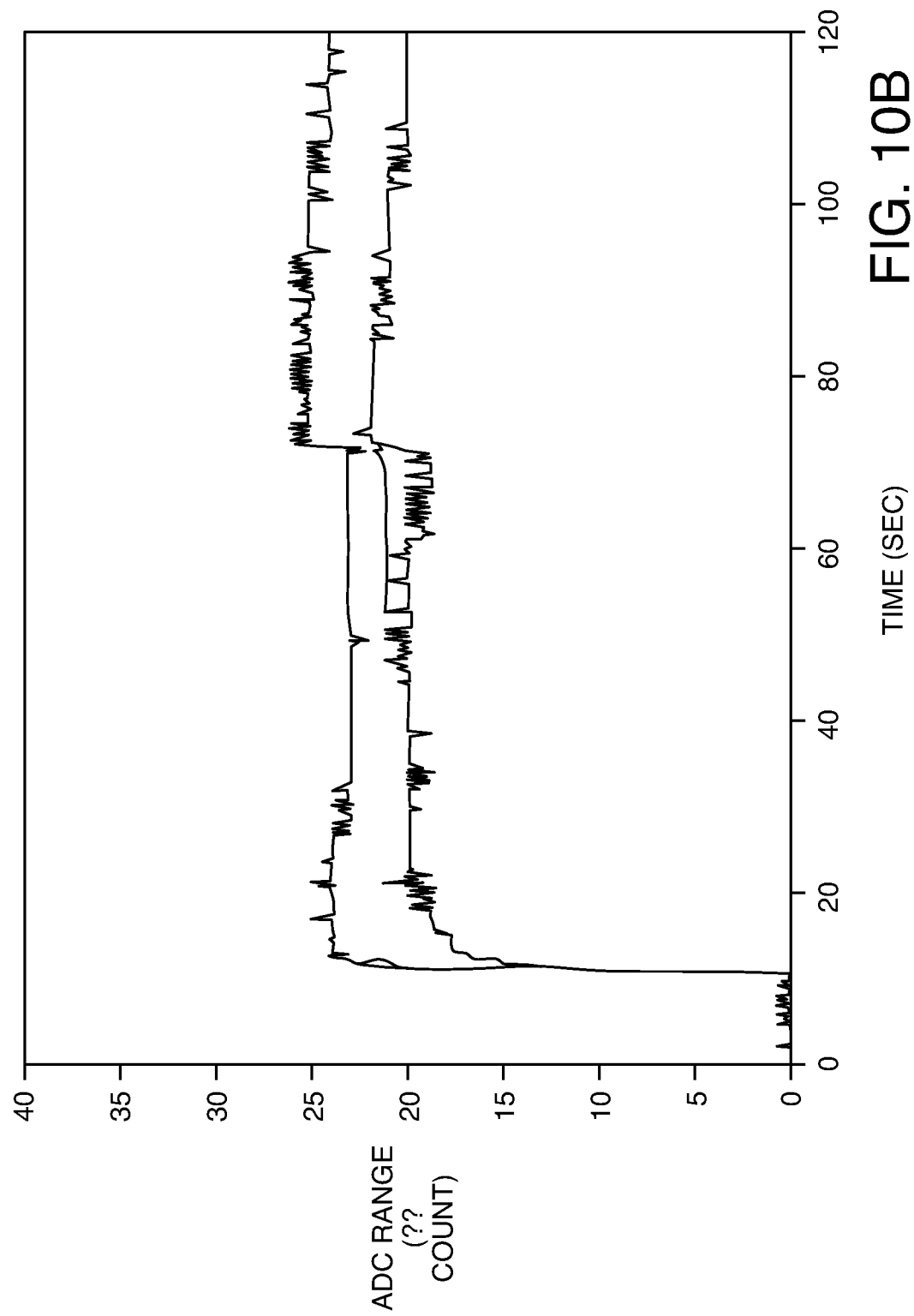
Figure 10C:
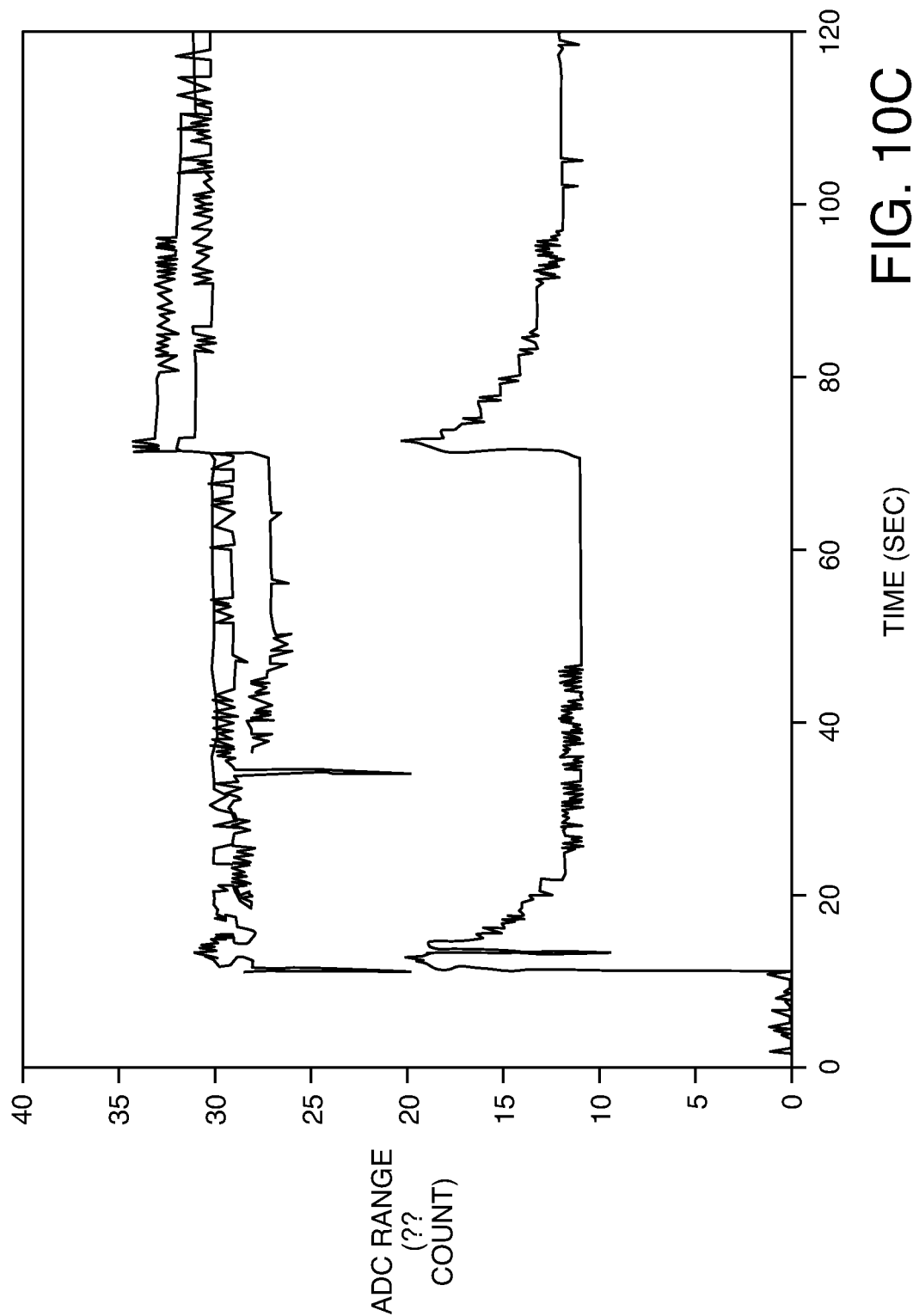
Figure 10D:
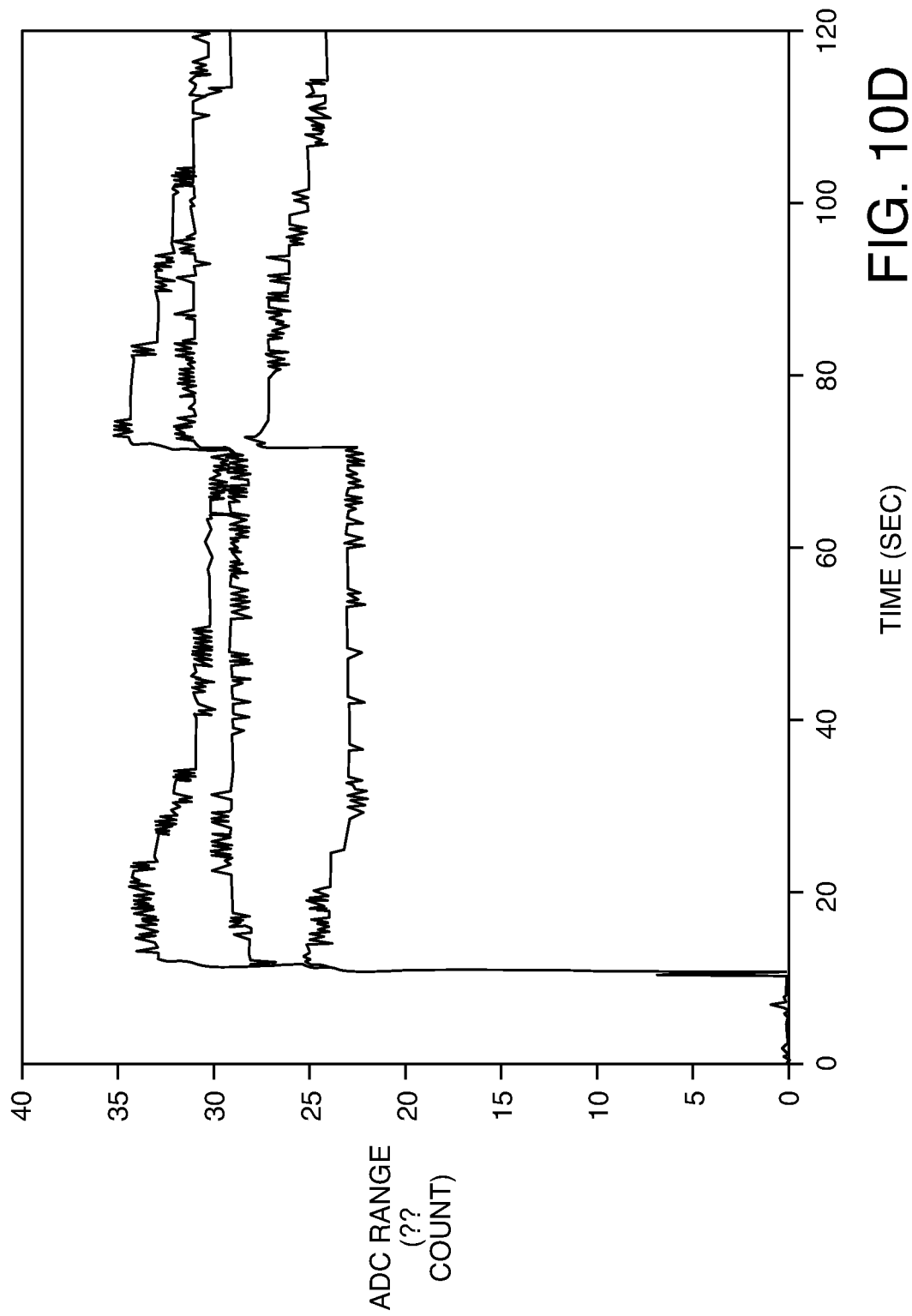

A third method measures the time taken to discharge a capacitor. A resistor-capacitor (RC) circuit has a characteristic discharge curve dependent on the capacitor under test. A system capable of measuring this time constant of this discharge curve can be used to detect the changes in the capacitance. A block diagram for such a system is illustrated in FIG. 9. In other words, as the capacitance of the system is different with an insulted absorbent article as compared to a dry absorbent article, the discharge curve will be different as well. In use, an open face virtual capacitor is manufactured using an RC circuit including a step function/pulse generator. The discharge time of the system capacitance is detected and processed using a digital signal processing (DSP) algorithm in a microcontroller. When insult conditions are reached, as determined by the microcontroller, an alarm signal is generated as further described herein.

FIG. 10 illustrates a representative set of sensor data in which a change in capacitance is detected when an absorbent article 20 is insulted. FIG. 10 also demonstrates the capability of detecting multiple insults.

Figure 11:
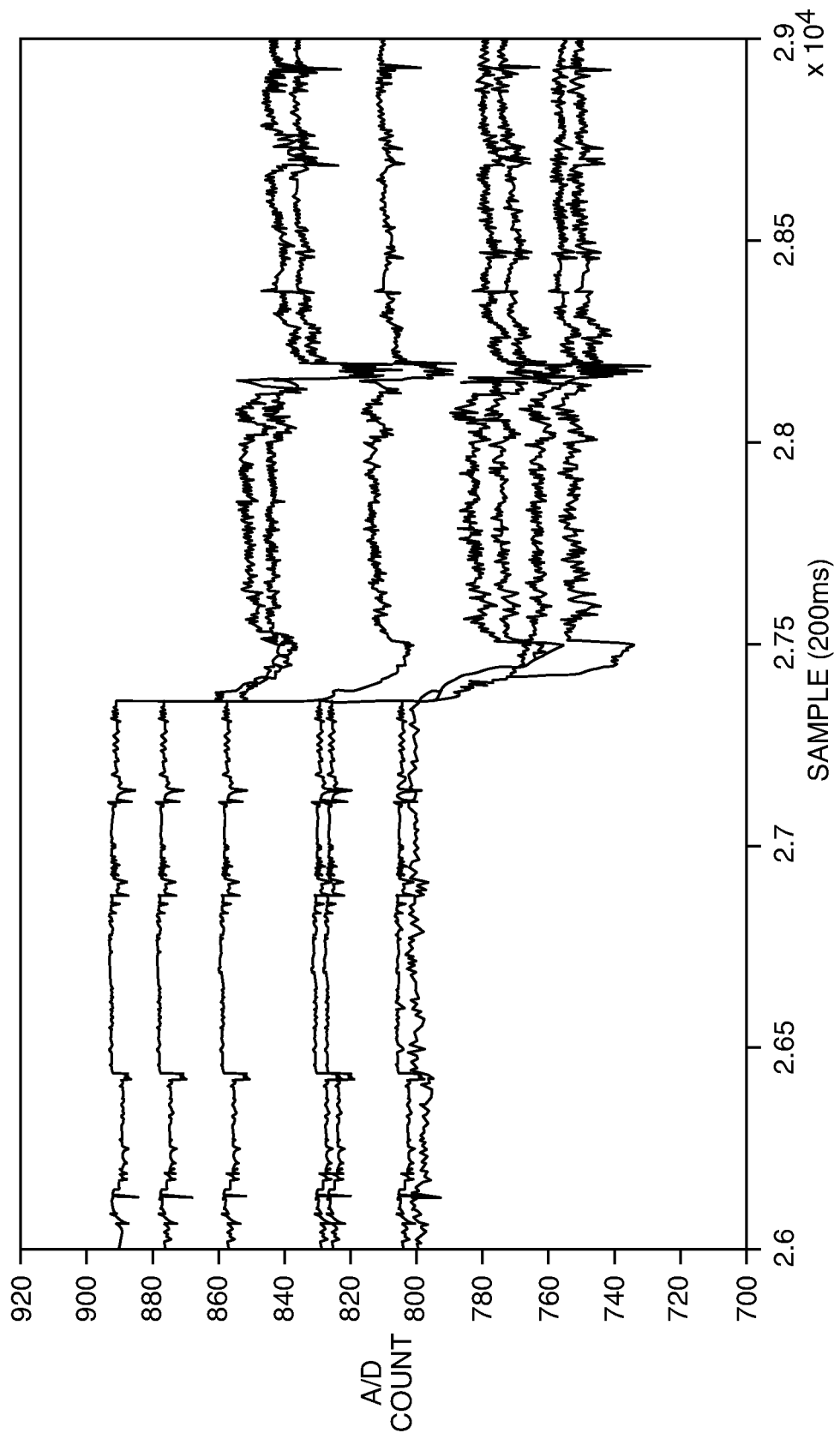
FIG. 11 illustrates an example of a similar set of data collected for children using a wetness indicator of the present disclosure.

FIG. 11 illustrates an example of a similar set of data collected for children of age 18-32 months, where sensors were attached to each child's absorbent article while data was being collected. These data also show a significant change in capacitance in presence of wetness.

Two algorithms were developed and implemented to detect wetness in the absorbent article 20: sensor-by-sensor detection and compare, and coherent addition.

A sensor-by-sensor detection and compare algorithm was developed and performed including the following steps:
1. Measure each sensor, and calculate a moving average baseline for each sensor.
2. Calculate the delta between the baseline and current sensor value.
3. If a sensor is above a threshold, an event timer begins.
    a. If the event timer does not time out, any samples above the threshold are counted
    b. If the event timer times out, a percentage of samples above the threshold are created and compared to a set value.
        i. If the value is above the set percentage, a void occurred.
        ii. If the value is below the set percentage, a void did not occur.
4. If a void is detected on a sensor in step 3, then look at the other present sensors to see if they detected a void as well. If the number of sensors that detected a void is greater than a set value (usually 50% of the number of sensors present) and happens within a set time of each other, a tone plays.
5. The algorithm continues to run, but the detection algorithm is disabled for a set amount of time.

This algorithm works well, but can be susceptible to movement noise. A window threshold can be created for all voids that occurred after the first void. This window helps filter out movement noise once the first void occurs. Using this algorithm requires a sensor line to be above a threshold for a certain time, and a percentage value must be above its threshold. Such percentage and time filter out fast-moving noise. The threshold should be approximately three or four counts for a 5 mil board, and six or seven counts for a 28 mil board.

A coherent addition algorithm uses less processing cycles because it does not require a moving average to be calculated for each sensor line, only one pseudo sensor line. A coherent addition algorithm was developed and performed including the following steps:
1. Measure each sensor and take the sum of present sensors.
2. Calculate a moving average baseline for the sum of the present sensors.
3. Calculate the delta between the baseline and sum of the present sensors.
4. If a delta is above a threshold, an event timer begins.
   a. If the event timer does not time out, any samples above the threshold are counted.
   b. If the event timer times out, a percentage of samples above the threshold is created and compared to a set value.
      i. If the value is above the set percentage, a void occurred, and a tone plays.
      ii. If the value is below the set percentage, a void did not occur.
5. The algorithm continues to run, but the detection algorithm is disabled for a set amount of time.
6. Repeat steps 1 through 3.
7. If a delta is within the multiple void window, an event timer begins.
   a. If the event timer does not time out, any samples above the threshold are counted.
   b. If the event timer times out, a percentage of samples above the threshold is created and compared to a set value.
      i. If the value is above the set percentage, a void occurred, and a tone plays
      ii. If the value is below the set percentage, a void did not occur.

The algorithm continues to run, but the detection algorithm can be disabled for a set amount of time. Upon detection, steps 6 and 7 run again.

The signaling device 110 can emit any suitable signal to indicate to the user that the absorbent article 20 has been insulted. The signal, for instance, can include an audible signal, a tactile signal, an electromagnetic signal, or a visual signal. The audible signal, for instance, can be as simple as a beep or can include a musical tune. In still another aspect, the signaling device can emit a wireless signal that then activates a remote device, such as a telephone or a pager.

Further aspects of the signaling device 110 can be found in co-pending U.S. patent application Ser. No. 12/347,539, entitled "Remote Detection Systems For Absorbent Articles," which is incorporated herein by reference to the extent it does not conflict herewith.

The electronics associated with the capacitive sensor 120 are relatively simple and can be miniaturized. The complete capacitive sensor 120 is disposed in a housing 135 (see FIG. 2) that is adapted to be attached to the absorbent article 20, or held in vicinity to the absorbent article 20. If the housing 135 is to be attached to the absorbent article 20 using an attachment mechanism, the housing 135 can be a pouch or a rigid or semi-rigid housing 135 that attaches to the outer cover 40 of the absorbent article 20 near the region where insults are expected. Such attachment mechanism can use adhesive, hook and loop, mechanical fasteners such as snaps, a clip, or a clasp, any other suitable attachment mechanism, or any combination of these. Various attachment mechanisms include those disclosed in co-pending and co-assigned U.S. Patent Application Publication No. 2007/0142797 to Long, et al. and entitled "Garments With Easy-To-Use Signaling Device"; U.S. Patent Application Publication No. 2006/0244614 to Long and entitled "Connection Mechanisms"; and U.S. Patent Application Publication No. 2007/0024457 to Long, et al. and entitled "Connection Mechanisms In Absorbent Articles For Body Fluid Signaling Devices" which are incorporated herein by reference to the extent they are consistent (i.e., not in conflict) herewith.

In another aspect of the present disclosure, the signaling device 110 is adapted to be held near the outermost surface of the outer cover 40 of the absorbent article 20. In this aspect, no attachment mechanism is needed. The wearer of the absorbent article 20 or a caregiver holds the signaling device 110 near the outer cover 40 of the absorbent article 20 to detect whether the absorbent article 20 has received an insult.

Sensors such as those described herein are further described, for instance, in U.S. patent application Ser. No. 11/511,583 and in U.S. Patent Application Publication No. 2008/0048786, which are both incorporated herein by reference to the extent they do not conflict herewith.

For example, in one aspect, the system can be configured such that the signaling device will not emit signals within a certain period of time once the system is first activated, where being activated means the system is in a condition to detect and provide a signal. The period of time can vary depending upon the particular circumstances and the particular application. For example, in one aspect, the system can be configured not to emit signals for at least the first 15 minutes, such as at least the first 30 minutes, such as at least the first 45 minutes, such as at least the first hour the absorbent article is worn.

In an alternative aspect, steady state is determined by the capacitive sensor 120 used in the system. Steady state can be determined when substantial or significant changes in capacitance fail to occur for a certain period of time indicating that steady state conditions have been reached. For instance, the system can be configured to only become activated once the capacitive sensor 120 determines no substantial changes within the interior of the article for a period of about five minutes, such as about 10 minutes, such as about 20 minutes, such as about 30 minutes, such as about 45 minutes, such as about one hour. For example, if the sensor is a capacitive sensor 120, steady state can be determined when the capacitive sensor 120 senses no more than about 5 percent change in capacitance on the interior of the article for a period of at least 10 minutes.

When using a capacitive sensor 120, the capacitive sensor 120 can be placed in any suitable location on the absorbent article 20. For instance, the capacitive sensor 120 can be placed in the crotch region 26, on the back region 24, or on the front region 22 of the article 20 depending upon various factors. As described herein, in certain applications, the capacitive sensor 120 can be placed on an exterior surface of the outer cover 40 of the absorbent article 20.

All of the sensors described herein can be configured to be disposed of with the absorbent article 20. When disposable, the capacitive sensor 120 can be integrated into the outer cover 40 of the absorbent article 20. For instance, in one aspect, the outer cover 40 can include more than one layer and the capacitive sensor 120 can be positioned in between the two layers.

In an alternative aspect, the capacitive sensor 120 can be configured to be removed from the absorbent article 20 when the absorbent article 20 is disposed and placed on a new absorbent article 20. In fact, in one aspect, the capacitive sensor 120 and/or signal device can include multiple settings depending upon the absorbent article 20 to which it is attached. In this manner, the signaling system can be modified based upon the particular product specifications. The product purchased can provide information to the consumer as to which setting to use.

As absorbent articles increase in effectiveness, in one aspect, the signaling system of the present disclosure can be configured to emit a signal or not emit a signal during a first insult of urine and/or to emit a signal when a second insult occurs. In one aspect, for instance, the absorbent article 20 can be constructed so as to be capable of holding two insults of urine from the wearer. A wetness sensing system can be particularly needed for these types of absorbent articles 20 so that a caregiver can differentiate between the first insult and the second insult. In accordance with the present disclosure, the signaling system can be constructed so as to recognize a change within the absorbent article 20 due to the first insult and then readjust the criteria based upon the second insult. Once the second insult is recognized, the signaling system can be designed to emit a signal.

For instance, after a first insult with urine, the capacitive sensor 120 can sense a change in capacitance within the absorbent article 20. The capacitive sensor 120 can also be configured to sense a change in capacitance after second and succeeding insults as well.

When using a capacitive sensor 120 as described herein, in one aspect, the system can be designed to take into account changes in the above measurements when the absorbent article 20 is first placed on the wearer. For example, when the absorbent article 20 is first donned, a change in capacitance can be expected. To account for this change, the system of the present disclosure can be configured to only cause signals to be emitted by the signaling device 110 when steady state conditions within the article have been reached.

In some instances, it is conceivable that the capacitive sensor 120 needs to contend with nearby objects that can cause interference. In practical applications, however, such a situation is unlikely because the interference-causing object typically needs to be very close to the capacitive sensor 120. This makes the appearance of an interference-causing object unlikely when the capacitive sensor 120 is used in conjunction with an absorbent article 20. Nevertheless, an interference problem of this sort can be managed by an intelligent algorithm that recognizes and stores signal output once the capacitive sensor 120 is in position and activated. The algorithm uses this signal output as a reference point and interprets subsequent signals in relation to this reference point. In other words, the algorithm includes an intelligent zeroing feature.

Once the device is activated, the algorithm takes a baseline measurement, which is automatic and transparent to the user. Once the signaling device 110 is installed by a user, the capacitive sensor 120 automatically zeroes itself to establish the point of zero wetness baseline needed.

In another aspect of the present disclosure (not shown), the signaling device 110 uses more than one capacitive sensor 120. For example, capacitive sensors 120 can be positioned such that one is near the front of the absorbent article 20 to detect urine and the other is near the rear of the absorbent article 20 to detect fecal matter.

These and other modifications and variations to the present disclosure can be practiced by those of ordinary skill in the art, without departing from the spirit and scope of the present disclosure, which is more particularly set forth in the appended claims. In addition, it should be understood that aspects of the various aspects can be interchanged both in whole and in part. Furthermore, those of ordinary skill in the art will appreciate that the foregoing description is by way of example only, and is not intended to limit the disclosure so further described in such appended claims.

What is claimed:

1. A signaling device for sensing and indicating the presence of a body exudate in an absorbent article, the device comprising:
    a housing;
    an attachment mechanism for removably attaching the housing to the absorbent article; and
    a capacitive sensor disposed within the housing, the capacitive sensor including an open face virtual capacitor having a ground plane positioned at a back of the sensor to prevent interference from a back side of the sensor wherein the capacitive sensor includes two open face virtual capacitors in an array and wherein the two open face virtual capacitors each have a diameter of 5 to 15 mm, wherein a spacing between the ground plane and the capacitors is 1 mm to 2.5 mm,
    wherein the signaling device is adapted to emit a signal when a change in a condition within the absorbent structure is sensed by the capacitive sensor.

2. The signaling device of claim 1, wherein the signaling device includes a plurality of settings that are selected by the user depending upon at least one specification of the absorbent article.

3. The signaling device of claim 1, wherein the signaling device is configured to differentiate between a first insult of the absorbent article with a body fluid from a second insult of the absorbent article with a body fluid.

4. The signaling device of claim 1, wherein the signaling device is configured to discern a steady state environment within the absorbent article after the article is donned before being configured to emit a signal by the signaling device.

5. The signaling device of claim 1, wherein the array includes 9 capacitors.

6. The signaling device of claim 1, wherein the array includes 6 capacitors.

7. The signaling device of claim 1, wherein the array includes 3 capacitors.

8. The signaling device of claim 1, wherein the array includes 5 capacitors.

9. The signaling device of claim 1, wherein the array includes 7 capacitors.

* * * * *